United States Patent [19]

Drake

[11] Patent Number: 4,559,111

[45] Date of Patent: Dec. 17, 1985

[54] AZEOTROPIC PURIFICATION OF Z-11-HEXADECENAL

[75] Inventor: Charles A. Drake, Nowata, Okla.

[73] Assignee: Phillips Petroleum Company, Bartlesville, Okla.

[21] Appl. No.: 684,208

[22] Filed: Dec. 20, 1984

[51] Int. Cl.$^4$ .................. B01D 3/36; C07C 47/21
[52] U.S. Cl. ........................ 203/57; 203/64; 203/80; 568/490; 568/492
[58] Field of Search .............. 568/492, 490, 462; 585/856, 864; 203/57, 64, 51, 56, 73, 80

[56] References Cited

U.S. PATENT DOCUMENTS

| | | |
|---|---|---|
| 2,580,750 | 1/1952 | Fleming . |
| 3,220,932 | 11/1965 | Crandall . |
| 3,894,916 | 7/1975 | Fischer et al. ............ 203/55 |
| 3,960,932 | 1/1976 | Heck .................... 568/490 |
| 4,170,601 | 10/1979 | Leadbetter ............. 568/492 |
| 4,335,263 | 6/1982 | Minai .................... 568/437 |
| 4,480,139 | 10/1984 | Scott et al. ............. 568/492 |

FOREIGN PATENT DOCUMENTS 857104 8/1981 U.S.S.R. .................. 568/490

Primary Examiner—Wilbur Bascomb
Attorney, Agent, or Firm—S. E. Reiter

[57] ABSTRACT

Production of essentially pure Z-11-hexadecenal by azeotropic distillation is described. Contacting a mixture of Z-11-hexadecenal, hexadecene and hexadecadiene with dimethylsulfoxide and subjecting the blend to azeotropic distillation allows for the removal of hydrocarbon impurities from the aldehyde. Contacting a mixture of Z-11-hexadecenal and hexadecenol with a $C_2$–$C_4$ glycol and subjecting the blend to azeotropic distillation conditions allows for the recovery of a glycol-aldehyde azeotrope from which essentially pure aldehyde is readily recovered. A mixture comprising Z-11-hexadecenal, hexadecene, hexadecadiene and hexadecenol can be sequentially treated according to the above-described azeotropic distillation steps in order to provide essentially pure Z-11-hexadecenal.

19 Claims, No Drawings

AZEOTROPIC PURIFICATION OF Z-11-HEXADECENAL

BACKGROUND

This invention relates to azeotropic distillation. In another aspect, this invention relates to azeotropic distillation of Z-11-hexadecenal. In yet another aspect, this invention relates to the separation of Z-11-hexadecenal/$C_{16}$-hydrocarbon mixtures. In another further aspect, this invention relates to the separation of Z-11-hexadecenal/hexadecenol mixtures. In a still further aspect, this invention relates to the separation of Z-11-hexadecenal, hexadecadiene, hexadecene and hexadecenol mixtures.

Z-11-Hexadecenal is a known pheromone for several insect species. In order to make this compound widely available for use in insect control, economic large scale synthetic conversion processes must be developed. While large scale reactions have been developed which permit the production of large quantities of Z-11-hexadecenal, the initially obtained product may contain reaction by-products, such as, for example, hexadecadiene, hexadecene and hexadecenol, which can be removed from the impure reaction product only with great difficulty. Thus, when it is attempted to purify Z-11-hexadecenal by distillation in the presence of the $C_{16}$-hydrocarbons, hexadecene and hexadecadiene, and/or hexadecenol, co-distillation of such impurities along with the desired aldehyde product is frequently a problem. Therefore, effective and economical large scale processes for the purification of Z-11-hexadecenal are desired.

OBJECTS OF THE INVENTION

An object of the invention is, therefore a process for the removal of hexadecene and hexadecadiene from a mixture of Z-11-hexadecenal, hexadecene and hexadecadiene.

Another object of the invention is a process for the removal of hexadecenol from a mixture of Z-11-hexadecenal and hexadecenol.

Yet another object of the invention is a process for the production of essentially pure Z-11-hexadecenal from a mixture comprising Z-11-hexadecenal, hexadecene, hexadecadiene and hexadecenol.

These and other objects of the invention will become apparent from the disclosure and claims provided herein.

STATEMENT OF THE INVENTION

In accordance with the invention, I have discovered that hexadecene and hexadecadiene can be azeotropically removed from mixtures of Z-11-hexadecenal, hexadecene and hexadecadiene in the presence of dimethylsulfoxide (DMSO). Thus, a hexadecene and hexadecadiene azeotrope can be collected as overhead leaving an essentially $C_{16}$-hydrocarbon-free distillation kettle bottom which can be further treated as required to recover the desired product, i.e., Z-11-hexadecenal.

In a further embodiment of the invention, Z-11-hexadecenal and hexadecenol can be separated by azeotropic distillation by distilling such a mixture in the presence of a $C_2$–$C_4$ glycol. The added azeotropic distillation solvent and the desired product, i.e., Z-11-hexadecenal, are recovered as distillation overhead while the alcohol impurity remains in the distillation kettle under the distillation conditions employed. Essentially pure Z-11-hexadecenal can then be readily recovered by collecting the upper phase of the distillation overhead.

In a still further embodiment of the invention, a mixture comprising Z-11-hexadecenal, hexadecene, hexadecadiene and hexadecenol can be separated to provide essentially pure Z-11-hexadecenal by first azeotropically distilling in the presence of DMSO, to remove hexadecene and hexadecadiene and then azeotropically distilling in the presence of a $C_2$–$C_4$ glycol, to allow Z-11-hexadecenal to be collected overhead essentially free of the hexadecenol impurity.

DETAILED DESCRIPTION OF THE INVENTION

In accordance with the present invention, a process for the production of essentially pure Z-11-hexadecenal from a mixture comprising Z-11-hexadecenal, hexadecene, hexadecadiene and hexadecenol is provided which comprises azeotropically distilling the mixture in the presence of dimethyl sulfoxide until the hexadecene and hexadecadiene have been azeotropically distilled from the mixture and then azeotropically distilling the distillation bottoms from the first step in the presence of $C_2$–$C_4$ glycol.

In accordance with another embodiment of the invention, a process is provided for the removal of hexadecene and hexadecadiene impurities from a mixture comprising Z-11-hexadecenal, hexadecene and hexadecadiene which comprises azeotropically distilling the mixture in the presence of dimethyl sulfoxide.

In accordance with yet another embodiment of the present invention, a process for the recovery of substantially pure Z-11-hexadecenal from a mixture comprising Z-11-hexadecenal and hexadecenol is provided comprising azeotropically distilling the mixture in the presence of $C_2$–$C_4$ glycol.

The Z-11-hexadecenal which can be subjected to the azeotropic distillation process of the present invention can be obtained from any suitable source. Those skilled in the art recognize that many different synthetic routes can be employed to prepare the desired product. Thus, for example 11-hexadecynal can be selectively hydrogenated to give Z-11-hexadecenal; Z-11-hexadecenol can be oxidized to give the desired aldehyde product and the like. A preferred source of the Z-11-hexadecenal to be purified in accordance with the present invention is the oxidation of a Z-11-hexadecenyl halide, e.g., Z-11-hexadecenyl bromide. This oxidation can be carried out, for example, in the presence of an amine oxide and sodium bicarbonate or dimethyl sulfoxide and sodium bicarbonate.

When Z-11-hexadecenal is prepared by the oxidation of a Z-11-hexadecenyl halide, common reaction by-products are hexadecenes and hexadecadienes, presumably formed by reduction and/or dehydrohalogenation of the starting material, and a hexadecenol presumably formed by hydrolysis of the halide starting material. A typical product mixture obtained when Z-11-hexadecenyl halide is oxidized to give Z-11-hexadecenal comprises:

$\geq$60 weight-% Z-11-hexadecenal, $\leq$20 weight-% hexadecenol and $\leq$10 weight-% hexadecene and hexadecadiene.

In order to azeotropically remove hexadecene and hexadecadiene from a mixture comprising Z-11-hexadecenal, hexadecene and hexadecadiene, the mixture is admixed with dimethylsulfoxide (DMSO) and subjected to azeotropic distillation conditions. The azeotropic distillation is preferably carried out until substantially all of the hexadecene and hexadecadiene have been removed overhead, leaving behind a bottom fraction essentially free of hexadecene and hexadecadiene While any amount of DMSO employed will aid in the azeotropic removal of hexadecene and hexadecadiene it is desired that at least enough DMSO be added so as to enable removal of substantially all of the above hexadecene and hexadecadiene from the mixture, and yet not so much DMSO be added so as to unduly increase the energy requirements or reduce the efficiency of the distillation process. It is of course recognized that DMSO need not be charged to the distillation kettle all at once, but instead can be added in small amounts (on a continuous or intermittent basis) during the course of the distillation until no more hexadecene and hexadecadiene are recovered overhead. In order to provide additional guidance, when DMSO is charged to the distillation kettle all at once, a weight ratio of DMSO to Z-11-hexadecenal of at least about 0.5:1 up to about 20:1 will generally be employed. Preferably, a weight ratio of 1:1 up to about 10:1 will be employed. Most preferably, a weight ratio of DMSO to Z-11-hexadecenal in the range of about 5:1 will be employed.

While those of skill in the art can readily determine suitable azeotropic distillation conditions for the recovery of DMSO-hexadecene and hexadecadiene azeotrope, the following values are suggested to provide additional guidance and because they afford readily attainable distillation conditions without the need for using special equipment.

|  | Temperature, °C. | Pressure, mm Hg |
|---|---|---|
| Broad | 50–200 | 20–200 |
| Intermediate | 100–160 | 60–100 |
| Preferred | 110–130 | 40–60 |

The separation of Z-11-hexadecenal and hexadecenol by azeotropic distillation involves the recovery of Z-11-hexadecenal overhead as an azeotrope with a $C_2$–$C_4$ glycol. Thus, a mixture comprising Z-11-hexadecenal and hexadecenol is contacted with $C_2$–$C_4$ glycol, and subjected to azeotropic distillation conditions. The azeotropic distillation can be carried out until substantially all Z-11-hexadecenal has been recovered overhead, leaving hexadecenol in the kettle bottom. While any amount of $C_2$–$C_4$ glycol employed will aid the azeotropic recovery of Z-11-hexadecenal, it is desired that at least enough glycol be employed to enable the azeotropic recovery of substantially all Z-11-hexadecenal in the mixture. On the other hand, the use of glycol in great excess will not provide any advantage in ultimate recovery of the desired product and instead will be wasteful of useful azeotroping agent and more costly to recover for recycle. As discussed above, it is not necessary to add all of the azeotropic agent to the distillation at once. Instead, glycol can be added in small amounts (on a continuous or intermittent basis) during the course of the distillation until no more Z-11-hexadecenal is recovered overhead. In order to provide additional guidance, when all glycol employed is charged to the distillation kettle at once, a weight ratio of glycol to Z-11-hexadecenal of about 1:1 up to about 10:1 will generally be employed. Preferably, a weight ratio of about 2:1 to about 8:1 and most preferably a weight ratio of glycol to Z-11-hexadecenal of about 5:1 will be employed.

Glycols contemplated to be useful in the practice of the present invention include ethylene glycol, propylene glycol, 1,4-butanediol and the like. Ethylene glycol is the presently preferred glycol because it gives excellent results, is relatively inexpensive and is readily available.

While those of skill in the art can readily determine suitable distillation conditions for recovery of Z-11-hexadecenal/glycol azeotrope, the following values are suggested to provide additional guidance and because they afford readily attainable distillation conditions without the need for special equipment.

|  | Temperature, °C. | Pressure, mm Hg |
|---|---|---|
| Broad | 60–160 | 2–150 |
| Intermediate | 90–125 | 10–50 |
| Preferred | 100–110 | 15–25 |

In accordance with another embodiment of the invention, Z-11-hexadecenal can be recovered in essentially pure form from a mixture comprising Z-11-hexadecenal, hexadecene, hexadecediene and hexadecenol by sequential azeotropic distillations as hereinabove described. Thus, the mixture is first contacted with DMSO and subjected to azeotropic distillation to remove hexadecene and hexadecadiene. The kettle bottoms are then contacted with $C_2$–$C_4$ glycol and subjected to azeotropic distillation conditions to recover Z-11-hexadecenal/glycol azeotrope overhead. Essentially pure Z-11-hexadecenal can then be recovered by collecting the upper layer of overhead from this second azeotropic distillation.

The following non limiting examples are provided to further illustrate my invention.

EXAMPLE I

Preparation of Z-11-Hexadecenal

A mixture of Z-11-hexadecenyl bromide (33 pounds; 50 mol) and DMSO (180 pounds; 1050 mol) was heated to 60° C. at 120 mm Hg under a slow-nitrogen flow for about 30 minutes. Then, sodium bicarbonate (18 pounds; 97 mol) and demethylphthalate (33 pounds; 77 mol) were added and the reaction temperature raised to 120° C. at 120 mm Hg and maintained for about 2 hours. The reaction mixture was cooled, washed with water, and the organic layer separated, dried and distilled. Analysis of the crude reaction produce showed about 68 percent Z-11-hexadecenal, 14 percent hexadecenol and about 2 percent hydrocarbon by-product (hexacecene plus hexadecadiene, the latter predominating). Analyses of the distillation fractions are summarized in Table I.

TABLE I

| Control Distillation of Crude Z-11-Hexadecenal | | | |
|---|---|---|---|
|  | Wt. | Product Analysis, % | | |
| Cut | recovered, pounds | Hydrocarbon by-product | Z-11-hexadecenal | Hexa-decenol |
| Feed | 25 | 2 | 68 | 14 |
| 1 | 0.6 | — | lights | — |
| 2 | 0.16 | 70 | 17 | 0 |
| 3 | 1.04 | 50 | 44 | 0 |
| 4 | 0.64 | 30 | 68 | 0.9 |
| 5 | 0.36 | 20 | 78 | 1.0 |
| 6 | 0.36 | 10 | 84 | 1.4 |
| 7 | 0.77 | 6 | 92 | 0.9 |

TABLE I-continued

<table>
<tr><th colspan="5">Control Distillation of Crude Z-11-Hexadecenal</th></tr>
<tr><th></th><th>Wt.<br>recovered,<br>pounds</th><th colspan="3">Product Analysis, %</th></tr>
<tr><th>Cut</th><th></th><th>Hydrocarbon<br>by-product</th><th>Z-11-hexadecenal</th><th>Hexa-<br>decenol</th></tr>
<tr><td>8</td><td>0.51</td><td>3</td><td>96</td><td>0.5</td></tr>
<tr><td>9</td><td>0.55</td><td>2</td><td>97</td><td>0.4</td></tr>
<tr><td>10</td><td>0.90</td><td>2</td><td>97</td><td>0.6</td></tr>
<tr><td>11</td><td>1.28</td><td><1</td><td>98</td><td>0.4</td></tr>
<tr><td>12</td><td>0.70</td><td><1</td><td>97</td><td>0.3</td></tr>
<tr><td>13</td><td>0.79</td><td><1</td><td>18</td><td>0.4</td></tr>
<tr><td>14</td><td>0.72</td><td><1</td><td>93</td><td>0.9</td></tr>
<tr><td>15</td><td>1.03</td><td><1</td><td>95</td><td>2.5</td></tr>
<tr><td>16</td><td>0.86</td><td><1</td><td>97</td><td>2.2</td></tr>
<tr><td>17</td><td>0.46</td><td><1</td><td>97</td><td>1.2</td></tr>
<tr><td>18</td><td>0.29</td><td><1</td><td>96</td><td>0.6</td></tr>
<tr><td>19</td><td>1.26</td><td><1</td><td>88</td><td>3.1</td></tr>
<tr><td>20</td><td>0.51</td><td><1</td><td>81</td><td>6.1</td></tr>
</table>

The reaction co-solvents dimethylphthalate and DMSO were largely removed as a separate layer before distillation, and residual amounts were removed as forerun in the distillation and, as a result, did not participate in or interfere with the product distillation. The distillation results indicate that about 11 pounds of Z-11-hexadecenal were recovered by distillation. However, the first 10 distillation fractions, in which greater than ⅓ of total recovered aldehyde was distilled, contained greater than 1 percent of the hydrocarbon by-products, hexadecene and hexadecadiene. In addition, the final 6 distillation fractions (accounting for over ⅓ of total aldehyde recovered by distillation) contained greater than 1 percent of the high boiling by-product, hexadecenol. Thus, standard distillation of crude Z-11-hexadecenal gives relatively pure product in only fractions 11–14. Of the 25 pounds of crude Z-11-hexadecenal charged to the distillation kettle, less than half was recovered by distillation (11.2 pounds or 45 percent) and of the material recovered overhead upon distillation, only about 30 percent (fractions 11–14) had less than 1 percent each of the low boiling impurities (hexadecene and hexadecadiene) and the high boiling impurities (hexadecenol).

EXAMPLE II

Azeotropic Distillation of Z-11-Hexadecenal with Dimethylsulfoxide

Twenty grams of crude hexadecenal containing about 68 percent hexadecenal, 14 percent hexadecenol and 2 percent hydrocarbon by-product was mixed with 100 grams of DMSO and distilled under reduced pressure (about 80 mm Hg) until substantially all of the hydrocarbon by-products (predominantly hexadecadiene and small amounts of hexadecene) were removed. Analyses of overhead fractions recovered at a head temperature of 116–117° C. are summarized in Table II.

TABLE II

<table>
<tr><th colspan="5">Invention Distillation with DMSO</th></tr>
<tr><th></th><th>Wt.<br>recovered,<br>g</th><th colspan="3">Product Analysis, %</th></tr>
<tr><th>Cut</th><th></th><th>Hydrocarbon<br>by-product</th><th>Z-11-hexadecenal</th><th>Hexa-<br>decenol</th></tr>
<tr><td>Feed</td><td>120</td><td>0.3</td><td>11.3</td><td>2.3</td></tr>
<tr><td>1</td><td>16.0</td><td>5.6</td><td>1.6</td><td>0.2</td></tr>
<tr><td>2</td><td>16.0</td><td>4.8</td><td>0.7</td><td>0.05</td></tr>
<tr><td>3</td><td>15.0</td><td>2.9</td><td>0.5</td><td>Trace</td></tr>
<tr><td>4</td><td>15.6</td><td>2.3</td><td>0.5</td><td>Trace</td></tr>
<tr><td>5</td><td>10.0</td><td>1.4</td><td>0.5</td><td>Trace</td></tr>
<tr><td>Kettle</td><td>46.1</td><td>0.8</td><td>62.1</td><td>12.0</td></tr>
</table>

TABLE II-continued

<table>
<tr><th colspan="5">Invention Distillation with DMSO</th></tr>
<tr><th></th><th>Wt.<br>recovered,<br>g</th><th colspan="3">Product Analysis, %</th></tr>
<tr><th>Cut</th><th></th><th>Hydrocarbon<br>by-product</th><th>Z-11-hexadecenal</th><th>Hexa-<br>decenol</th></tr>
<tr><td>bottom</td><td></td><td></td><td></td><td></td></tr>
</table>

This example demonstrates that the hydrocarbon by-products, hexadecene and hexadecadiene, can be reduced to very low levels by azeotropic distillation of crude Z-11-hexadecenal with DMSO. An added advantage of this means of removing hydrocarbon impurities is the very small sacrifice of the desired aldehyde upon removal of the hydrocarbon impurities. The kettle bottoms which result from the DMSO azeotropic distillation can now be further distilled without the interference by the hydrocarbon impurities observed in Example I, i.e., azeotrope of hydrocarbon impurities with Z-11-hexadecenal. The other major by-product, hexadecenol, can then be separated from the resulting mixture by the azeotropic distillation described in Example III.

EXAMPLE III

Azeotropic Distillation of Z-11-Hexadecenal with Glycols

Ten grams of crude hexadecenal (analysis of feed indicated in Table III) was mixed with varying amounts of a glycol, and the mixture distilled at about 20 mm Hg. Analyses of distillation feeds, top and bottom layers of distillation fractions recovered and distillation kettle bottoms are summarized in Table III.

TABLE III

<table>
<tr><th colspan="6">Invention Distillation with Glycols</th></tr>
<tr><th>Run number;<br>distillation<br>cut number:</th><th>Azeotropic<br>solvent, g</th><th>Azeotropic<br>solvent</th><th colspan="3">GLC Analysis, %</th></tr>
<tr><th></th><th></th><th></th><th>HC</th><th>HDA</th><th>HD-ol</th></tr>
<tr><td>1-Feed</td><td>Ethylene<br>glycol, 50</td><td></td><td>~9</td><td>61.2</td><td>10.3</td></tr>
<tr><td>1,1-top</td><td></td><td>2.9</td><td>21.2</td><td>69.2</td><td>2.8</td></tr>
<tr><td>-bottom</td><td></td><td>93.1</td><td>0.9</td><td>3.9</td><td>0.4</td></tr>
<tr><td>1,2-top</td><td></td><td>1.9</td><td>11.6</td><td>78.5</td><td>3.7</td></tr>
<tr><td>-bottom</td><td></td><td>95.3</td><td>0.3</td><td>3.5</td><td>0.5</td></tr>
<tr><td>1,3-top</td><td></td><td>2.5</td><td>4.4</td><td>81.8</td><td>4.2</td></tr>
<tr><td>-bottom</td><td></td><td>96.8</td><td>0</td><td>2.9</td><td>0.4</td></tr>
<tr><td>1-kettle-top</td><td></td><td>7.9</td><td>0</td><td>61.3</td><td>3.0</td></tr>
<tr><td>-bottom</td><td></td><td>93.8</td><td>0</td><td>3.8</td><td>1.2</td></tr>
<tr><td>2-Feed</td><td>Ethylene<br>glycol, 100</td><td></td><td>6.0</td><td>48.4</td><td>4.0</td></tr>
<tr><td>2,1-top</td><td></td><td>1.5</td><td>9.9</td><td>75.3</td><td>1.3</td></tr>
<tr><td>-bottom</td><td></td><td>87.7</td><td>0</td><td>2.8</td><td>0.1</td></tr>
<tr><td>2,2-top</td><td></td><td>1.5</td><td>6.5</td><td>80.6</td><td>1.7</td></tr>
<tr><td>-bottom</td><td></td><td>95.5</td><td>0</td><td>2.8</td><td>0.1</td></tr>
<tr><td>2,3-top</td><td></td><td>1.6</td><td>3.5</td><td>83.6</td><td>1.9</td></tr>
<tr><td>-bottom</td><td></td><td>94.6</td><td>0</td><td>3.5</td><td>0.2</td></tr>
<tr><td>2,4-top</td><td></td><td>1.7</td><td>1.6</td><td>84.9</td><td>2.2</td></tr>
<tr><td>-bottom</td><td></td><td>94.4</td><td>0</td><td>4.1</td><td>0.2</td></tr>
<tr><td>2,5-top</td><td></td><td>1.5</td><td>0.6</td><td>84.9</td><td>2.6</td></tr>
<tr><td>-bottom</td><td></td><td>95.9</td><td>0</td><td>2.7</td><td>0.2</td></tr>
<tr><td>2-kettle-top</td><td></td><td>3.3</td><td>0.11</td><td>62.3</td><td>10.5</td></tr>
<tr><td>-bottom</td><td></td><td>90.4</td><td>0</td><td>6.4</td><td>1.0</td></tr>
<tr><td>3-Feed</td><td>1,4-butanediol,<br>75</td><td></td><td>~9</td><td>61.2</td><td>10.3</td></tr>
<tr><td>3,1-top</td><td></td><td>ND**</td><td>16.7</td><td>24.4</td><td>1.2</td></tr>
<tr><td>-bottom</td><td></td><td>76.8</td><td>2.9</td><td>3.8</td><td>0.4</td></tr>
<tr><td>3,2-top</td><td></td><td>4.7</td><td>3.4</td><td>73.5</td><td>4.3</td></tr>
<tr><td>-bottom</td><td></td><td>55.6</td><td>1.5</td><td>32.3</td><td>2.2</td></tr>
<tr><td>3,3-top</td><td></td><td>0.9</td><td>0.6</td><td>71.2</td><td>5.9</td></tr>
<tr><td>-bottom</td><td></td><td>88.9</td><td>0</td><td>6.9</td><td>1.3</td></tr>
<tr><td>3,4-top</td><td></td><td>5.4</td><td>0</td><td>52.7</td><td>8.7</td></tr>
<tr><td>-bottom</td><td></td><td>72.8</td><td>0</td><td>15.5</td><td>3.7</td></tr>
<tr><td>3,5-top***</td><td></td><td>—</td><td>—</td><td>—</td><td>—</td></tr>
</table>

TABLE III-continued

Invention Distillation with Glycols

| Run number; distillation cut number: | Azeotropic solvent, g | Azeotropic solvent | GLC Analysis, % | | |
|---|---|---|---|---|---|
| | | | HC | HDA | HD-ol |
| -bottom | | 86.8 | 0 | 2.6 | 2.5 |
| 3-kettle-top | | 16.8 | 0 | 41.6 | 32.1 |
| -bottom | | 80.8 | 0 | 2.9 | 11.6 |

*HC = Hydrocarbon by-product
HDA = Z-11-Hexadecenal
HD-ol = Hexadecenol
**ND = Not determined
***there was no phase separation in this fraction These examples demostrate that azeotropic distillation of crude Z-11-hexadecenal greatly reduces the amount of hexadecenol impurity in the aldehyde. This is important because the alcohol would otherwise co-distill with the aldehyde, as demonstrated in Example I. After removal of the hexadecenol as described above, and removal of hydrocarbon impurities as described in Example II, the resulting Z-11-hexadecenal can be subjected to fractional distillation to provide substantially pure Z-11-hexadecenal, for use, for example, as a pheromone.

The examples have been provided merely to illustrate the practice of my invention and should not be read so as to limit the scope of my invention or the appended claims in any way. Reasonable variation and modification, not departing from the essence and spirit of my invention, are contemplated to be within the scope of patent protection desired and sought.

That which is claimed:

1. A process for the production of essentially pure Z-11-hexadecenal from a mixture comprising Z-11-hexadecenal, hexadecene, hexadecadiene and hexadecenol which comprises:
   (a) azeotropically distilling said mixture in the presence of dimethyl sulfoxide (DMSO) at least until said hexadecene and hexadecadiene have been azeotropically distilled from said mixture; and
   (b) azeotropically distilling the distillation bottoms from step (a) in the presence of a $C_2$–$C_4$ glycol.

2. A process in accordance with claim 1 wherein the weight ratio of DMSO to Z-11-hexadecenal is at least 1:1 and no greater than about 20:1.

3. A process in accordance with claim 1 wherein the weight ratio of $C_2$–$C_4$ glycol to Z-11-hexadecenal is at least 1:1 and no greater than about 10:1.

4. A process in accordance with claim 1 wherein the azeotropic distillation conditions in step (a) comprise a pot temperature of about 50 to about 200° C. at a pressure of about 1–600 mm Hg.

5. A process in accordance with claim 1 wherein said $C_2$–$C_4$ glycol is ethylene glycol.

6. A process in accordance with claim 5 wherein said azeotropic distillation conditions in step (b) comprise a pot temperature of about 60 to about 160° C. at a pressure of about 2–150 mm Hg.

7. A process in accordance with claim 1 wherein said mixture comprising Z-11-hexadecenal, hexadecene, hexadecadiene and hexadecenol is obtained by the conversion of Z-11-hexadecenyl bromide to Z-11-hexadecenal in the presence of dimethylsulfoxide and NaHCO$_3$.

8. A process in accordance with claim 1 wherein said mixture comprising Z-11-hexadecenal, hexadecene, hexadecadiene and hexadecenol and comprises:
   $\geq$60 wt. % Z-11-hexadecenal,
   $\leq$10 wt. % hexadecene plus hexadecadiene and
   $\leq$20 wt. % hexadecenol.

9. A process in accordance with claim 1 further comprising:
   (c) recovering the upper layer from the overhead fraction obtained in step (b) as substantially pure Z-11-hexadecenal.

10. A process for the removal of hexadecene and hexadecadiene impurities from a mixture comprising Z-11-hexadecenal, and hexadecene and hexadecadiene which comprises:
    azeotropically distilling said mixture in the presence of dimethyl sulfoxide (DMSO) at least until said hexadecene and hexadecadiene have been azeotropically distilled out of said mixture.

11. A process in accordance with claim 10 wherein the weight ratio of DMSO to Z-11-hexadecenal is at least 1:1 and no greater than about 20:1.

12. A process in accordance with claim 10 wherein said mixture comprising Z-11-hexadecenal and hexadecene and hexadecadiene comprises:
    $\geq$60 weight % Z-11-hexadecenal and
    $\leq$10 wt % hexadecene and hexadecadiene.

13. A process in accordance with claim 10 wherein the weight ratio of said mixture comprising Z-11-hexadecenal, hexadecene and hexadecadiene is at least about 12:1 (Z-11-hexadecenal to hexadecene plus hexadecadiene).

14. A process in accordance with claim 10 wherein the azeotropic distillation conditions comprise a pot temperature of about 50 to about 200° C. at a pressure of about 1–600 mm Hg.

15. A process for the recovery of substantially pure Z-11-hexadecenal from a mixture comprising Z-11-hexadecenal and hexadecenol which comprises azetropically distilling said mixture in the presence of a $C_2$–$C_4$ glycol.

16. A process in accordance with claim 15 further comprising:
    recovering the upper layer from the overhead fraction of the azeotropic distillation which consists essentially of substantially pure Z-11-hexadecenal.

17. A process in accordance with claim 15 wherein the weight ratio of $C_2$–$C_4$ glycol to Z-11-hexadecenal is at least 1:1 and no greater than about 10:1.

18. A process in accordance with claim 15 wherein said $C_2$–$C_4$ glycol is ethylene glycol.

19. A process in accordance with claim 18 wherein the azeotropic distillation conditions comprise a pot temperature of about 60 to about 160° C. at a pressure of about 2–150 mm Hg.

* * * * *